United States Patent [19]

Scheidl et al.

[11] 4,122,064

[45] Oct. 24, 1978

[54] NOVEL ORGANO-TIN COMPOUNDS AND THEIR USE AS STABILIZERS

[75] Inventors: Franz Scheidl, Gersthofen; Hans Huber, Burgkirchen, Alz; Klaus Ulm, Burghausen, Salzach; Harald Häberlein, Gersthofen; Gerhard Pfahler, Augsburg, all of Fed. Rep. of Germany

[73] Assignee: Hoechst Aktiengesellschaft, Frankfurt am Main, Fed. Rep. of Germany

[21] Appl. No.: 752,428

[22] Filed: Dec. 20, 1976

[30] Foreign Application Priority Data

Dec. 30, 1975 [DE] Fed. Rep. of Germany ....... 2559201

[51] Int. Cl.² .............................................. B01F 7/02
[52] U.S. Cl. ............................ 260/45.75 S; 252/406; 260/429.7
[58] Field of Search ...................... 260/429.7, 45.75 S; 252/406

[56] References Cited

U.S. PATENT DOCUMENTS

| | | | |
|---|---|---|---|
| 2,648,650 | 8/1953 | Weinberg et al. | 260/429.7 |
| 3,565,931 | 2/1971 | Brecker | 260/429.7 |
| 3,640,953 | 2/1972 | Brecker et al. | 260/45.75 S |
| 3,665,024 | 5/1972 | Oakes et al. | 260/429.7 |
| 3,845,017 | 10/1974 | Collins et al. | 260/45.75 K |
| 3,931,262 | 1/1976 | Wirth et al. | 260/429.7 |

FOREIGN PATENT DOCUMENTS

2,558,729 12/1975 Fed. Rep. of Germany ........... 560/147

OTHER PUBLICATIONS

Kirk–Othmer Encyclopedia of Chemical Technology 8, 269-270 (1965).

*Primary Examiner*—Helen M. S. Sneed
*Attorney, Agent, or Firm*—Connolly and Hutz

[57] ABSTRACT

The present invention provides novel organo-tin compounds of the formula

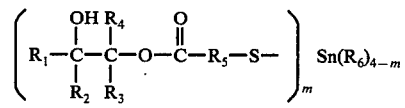

and their use as stabilizers for halogen containing polymers. As compared to the known tin stabilizers, the tin compounds of the invention have improved stabilizing properties at identical tin content.

4 Claims, No Drawings

NOVEL ORGANO-TIN COMPOUNDS AND THEIR USE AS STABILIZERS

Halogen containing polymers, especially polymers and co-polymers of vinyl chloride, are prone to degradation under the influence of heat and light, which results in discoloration, brittleness and general deterioration of the mechanical properties. It is therefore necessary to add light and heat stabilizers to such plastics in order to prevent or at least substantially retard their degradation.

Generally, lead salts of organic and/or inorganic acids, barium, cadmium, calcium, zinc and other metal salts of organic acids or other hydrogen acidic compounds, for example phenols and acidic esters, and organo-tin compounds are used as heat stabilizers. In order to improve the activity of these stabilizers, also called primary stabilizers, costabilizers are often added to them, for example organic phosphites, epoxy compounds, or polyols.

Most active heat stabilizers for halogen containing polymers are organol-tin compounds, especially those which contain tin-sulfur bonds, for example dioctyl-tin-bis-thioglycolic acid iso-octyl ester. The requirements to be met by the stabilizing additives become more and more severe along with the rising speeds and temperatures in the processing of the cited polymers and with the demands regarding aspect and utilitarian properties of the final products; these requirements relate to an intensified stabilizing activity (starting color and long duration heat stability) and a reduced tendency of the plastic compositions to stick onto the shaping parts of the processing machines.

An increased concentration of the commercial organo-tin compounds in the halogen containing polymers is no acceptable solution for the industrial practice because of the price of this class of compounds on the one hand and on the other because of the quantitative limits set by legal prescription (for example in the field of food packages).

It is therefore an object of the present invention to provide stabilizers on the basis of organo-tin compounds which, at identical tin content in the formulation as compared to tin stabilizers hitherto known, have improved stabilizing properties and thus meet the above requirements.

Suprisingly, it has been found that the hitherto unknown organo-tin salts of mercaptocarboxylic acid-$\beta$-hydroxy esters substantially possess the intended favorable properties.

The present invention provides therefore novel organo-tin compounds of the formula

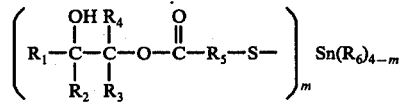

wherein $R_1$ through $R_4$, being identical or different, each represent
(a) from 0 to 3 hydrogen atoms,
(b) a phenyl radical or a cycloakyl or cycloalkylene radical having from 5 to 12 carbon atoms, these radicals optionally being substituted by alkyl groups having from 1 to 9 carbon atoms, halogen or —OH,
(c) a linear or branched akyl radical having from 1 to 100 carbon atoms, optionally substituted by a phenyl, a $C_1$-$C_9$-alkylphenyl, a cycloalkyl or cycloalkylene group having from 5 to 12 carbon atoms;
the radicals cited sub (b) and (c) optionally containing ether, thioether, carboxylic acid ester or epoxide groups, halogen substituents and C=C bonds in addition, and/or $R_2$ and $R_3$ being common members of a saturated or unsaturated, optionally alkyl- or aryl-substituted alkylene chain having from 3 to 10 carbon atoms; and the sum of all carbon atoms contained in the radicals $R_1$ through $R_4$ being superior to 2 and up to 100;

$R_5$ is an arylene group or a saturated or unsaturated, optionally alkyl- or phenyl-substituted alkylene group having from 1 to 12 carbon atoms in the alkylene chain, the alkyl substituents possibly present in the alkylene chain optionally containing carboxylic acid ester groups, $R_6$ is a linear or branched alkyl radical having from 1 to 30 carbon atoms, a vinyl, allyl, aralkyl, aryl or cycloalkyl radical having from 5 to 8 carbon atoms, and $m$ is 1, 2 or 3.

This invention relates furthermore to the use of the above organo-tin compounds as stabilizers for organic polymers and the polymers thus stabilized.

The organo-tin compounds of the invention which contain a 2-hydroxy-alcohol as alcoholic component are far superior to those obtained from mercaptocarboxylic acid esters of polyols such as ethyleneglycol, propyleneglycol or the ethoxylation products thereof, butyleneglycol, hexyleneglycol, glycerol, trimethylolpropane, pentaerythritol etc. . and known from the literature with respect to their stabilizing properties in plastics. While the known compounds which are described for example in German Offenlegungsschriften Nos. 1,418,001, 1,958,744 and 2,334,833, British patent specification No. 1,027,718, U.S. Pat. Spec. No. 3,632,538 and French patent specification No. 2,023,955 are difficult to handle because of their partially rubberlike state of aggregate, and cause undesirable sticking of the plastic compositions containing them to the processing machines, the highly efficient stabilizers of this invention, especially those wherein the radicals $R_1$ through $R_4$ contain a high number of carbon atoms, ensure a considerably reduced or even totally suppressed tendency to sticking, so that also the formation of deposits in the processing machines and thus scoring is prevented to a large extent. A further advantage resides in the fact that those representatives of the stabilizers of the invention which are solid at room temperature maintain the processing thermostability of the plastic compositions containing them better than the known liquid tin stabilizers. Moreover, the substances of the invention are practically non-volatile. Very advantageous is furthermore the possibility of varying the tin content of the novel stabilizing compounds within wide limits, since the corresponding starting substances having a broad range of carbon atoms are easily obtainable, so that the most different requirements of the practice can be met without difficulty.

Some of the tin stabilizers of the invention are still liquid at room temperature; generally and preferably, however, the novel organo-tin compounds are solid, white products part of which even have a wax-like nature. These latter ones having flow points/drop points of from 35° to 100° C are especially interesting, since, in addition to their excellent stabilizing effect, they have a favorable influence on the properties of the polymer compositions, as already mentioned above.

The symbols $R_1$ through $R_4$ of the formula

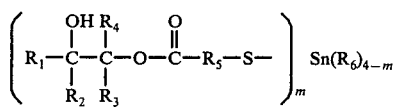

which is characteristic for the novel tin compounds represent each from 0 to 3 hydrogen atoms, a phenyl radical optionally substituted by preferably one or two alkyl groups having from 1 to 9 carbon atoms, halogen, preferably chlorine or -OH, or a saturated or unsaturated cycloalkyl or cycloalkylene radical having from 5 to 12, preferably from 5 to 10 carbon atoms and being unsubstituted or substituted as indicated before, for example phenyl, tolyl, xylyl, t-butylphenyl, nonylphenyl, chlorophenyl, hydroxyphenyl, cyclopentyl, -hexyl, -heptyl, -octyl or -dodecyl radicals. The symbols may also represent each a linear or branched alkyl radical having from 1 to 100, preferably from 6 to 60, and especially from 8 to 40, carbon atoms, optionally substituted by a phenyl group, a $C_1$-$C_9$-alkylphenyl group or a cycloalkyl or cycloalkylene group having from 5 to 12, preferably from 5 to 10, carbon atoms. Furthermore, the radicals $R_1$ through $R_4$ may contain ether, thioether, carboxylic acid ester of epoxide groups, halogen substituents, preferably chlorine, and C=C bonds, that is, —O—, —S— or —CO—O— may be inserted into an alkyl chain. Examples are $R_1$ (and/or $R_2$, $R_3$, $R_4$) being —$CH_2$—O—R, —$CH_2$—O—COR or —$CH_2$—S—R, R representing an alkyl radical such as hexyl, dodecyl or octadecyl etc., or an aryl radical such as phenyl, totyl, nonylphenyl etc. As examples for an interruption of the alkyl chain in the substituents $R_1$ through $R_4$ by an epoxy group those compounds may be cited which are formed when mercaptocarboxylic acids are reacted with only one of the three epoxy groups present in epoxidized soybean oil.

$R_2$ and $R_3$ may furthermore be common members of a saturated or unsaturated, optionally alkyl- or arylsubstituted alkylene chain having from 3 to 10, preferably 3 to 8, carbon atoms. In this case, the organo-tin compounds of the invention are derived from esters the alcoholic component of which is for example a α-hydroxycyclopentyl, β-hydroxycyclohexyl or α-hydroxycyclooctyl radical. In compounds of this structure, $R_1$ and $R_4$ are preferably hydrogen.

The radicals $R_1$ through $R_4$ may be identical or different; however, as already mentioned, only three of them at most can be hydrogen. A further limit is set by the fact that the sum of all carbon atoms contained in the radicals $R_1$ through $R_4$ must be superior to 2, but may be up to 100, preferably up to 60.

Preferred organo-tin compounds are those where $R_1$ is derived from linear, aliphatic hydrocarbons having from 6 to 58, preferably 8 to 40, and especially 12 to 36, carbon atoms, and $R_2$ through $R_4$ each are hydrogen, methyl or ethyl.

$R_5$ represents an arylene group having advantageously 6 to 12 carbon atoms, for example a p-phenylene or 1,2-naphthylene group, or a saturated or unsaturated alkylene group having from 1 to 12, preferably 1 to 5, and especially 1 or 2, carbon atoms in the alkylene chain. The alkylene chain may contain phenyl or alkyl substituents having from 1 to 16, preferably 1 to 6, and especially 1 to 4, carbon atoms; furthermore, the alkyl or phenyl substituents of the alkylene chain may have carboxylic acid ester groups derived from polybasic mercaptocarboxylic acids and the partial ester thereof.

$R_6$ represents a linear or branched alkyl radical having from 1 to 30, preferably from 1 to 10, carbon atoms, such as methyl, ethyl, propyl, i-butyl, i-pentyl, hexyl, 2-ethylhexyl, nonyl, dodecyl etc., a vinyl, allyl, aralkyl radical such as benzyl, an aryl radical such as phenyl or naphthyl, or a cycloalkyl radical having from 5 to 8 carbon atoms. Preferred are methyl, butyl or octyl.

The novel compounds contain at least one, preferably 2 or 3, and especially 2, sulfur/tin bonds, which corresponds to the formula wherein $m$ is 1, 2 or 3.

The organo-tin compounds of the invention are manufactured according to known methods by reaction of suitable tin compounds containing the radical $R_6$, preferably halides such as chlorides or bromides or oxides, with mercaptocarboxylic acid 2-hydroxy ester of the structure

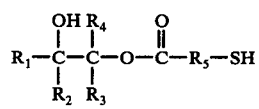

wherein $R_1$ through $R_5$ are as defined above.

This reaction may for example be carried out at temperatures of from 50° to 120°C, optionally in the presence of an inert solvent, for example an aliphatic or aromatic hydrocarbon, within about 1 to 5 hours. When a corresponding tin halide is used as starting material, the addition of a HCl acceptor such as alkali metal hydroxides, carbonates or amines is recommended.

The above mercaptocarboxylic acid esters for their part are obtained for example by reaction of epoxides of the structure

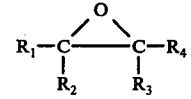

with mercaptocarboxylic acids of HOOC-$R_5$-SH structure according to the indications of German Offenlegungsschrift No. 2,558,729.

Suitable mercaptocarboxylic acids are for example mercaptoacetic acid, 2- and 3mercaptopropionic acid, 2-, 3- and 4-mercaptobutyric acid, 2-mercaptovaleric acid, ω-mercaptohexanoic acid, 3-mercapto-4-ethylenehexanoic acid, 4-mercaptocaproic acid, 3-mercapto-2,3-dimethylbutyric acid, 3-mercapto-4-hydroxybutyric acid, 2-mercapto-3-methylbutyric acid, 3-mercapto-4,5-dimethylhexanoic acid, 2-mercaptolauric acid, 2-mercapto-oleic acid, 2-mercaptostearic acid, thiomalic acid and the semiesters thereof, 2- and 3-mercaptoglutaric acid and the semiesters thereof, thiocitric acid and the partial esters thereof, dithiolactic acid, 2-mercaptopimelic acid and the semiesters thereof, 2-mercaptosuberic acid and the semiesters thereof, thiosalicylic acid and 3-mercapto-2-naphthoic acid; mercaptoacetic and 3-mercaptopropionic acid being preferred.

Suitable epoxides are for example epoxidized olefins such as 2,3-epoxypentane, but especially epoxidized α-olefins such as 1,2epoxyhexane, -octane, -dodecane, -octadecane; or long-chain epoxides or epoxide mixtures, for example those of $C_{20}$ to $C_{24}$, $C_{20}$ to $C_{28}$, $C_{26}$ to $C_{52}$, or $C_{30+}$ α-olefin fractions obtainable e.g. according to the Ziegler synthesis; furthermore arylsubstituted epoxides such as styrene oxide, tri- and tetraphenylethylene oxide; glycidyl ethers of alcohols and phenols such as octanol, octadecanol, phenol or nonylphenol; glycidyl-thioethers of mercaptans such as octanethiol, dodecanethiol, octadecane-thiol or thiophenol; glycidyl esters of carboxylic acids such as octanoic, lauric, stearic, benzoic, p-hydroxybenzoic or p-t-butylbenzoic acid; epoxidized fatty acid esters such as 9,10-epoxystearic acid esters; epoxidized natural oils such as epoxidized castor oil or soybean oil, only one epoxide groups per molecule contained in these oils being reacted with the mercaptocarboxylic acid; 9,10-epoxyoctadecanol, 2,3-epoxy-2,6-dimethyloctene-(7)-ol-6); epoxy-2,6-dimethyloctadiene, 4,5-epoxyhexenic acid-(2) methyl ester; cylic epoxides such as epoxycyclopentane, -hexane, -octane; epoxycyclooctatriene, 1,2- and 2,3-epoxytetraline, 3,4 -epoxytricyclo- (0,3,4,1)-decene (obtainable from dicyclopentadiene), or hexachloro-2,3-epoxynorbornene. Especially suitable epoxides are cheap industrial grade products such as glycidyl ethers, -esters and -thioethers, especially epoxidized fatty acids and fatty acid esters and epoxidized α-olefins.

The mercaptocarboxylic acid esters are for example prepared as follows: The components are allowed to react, with agitation, at temperatures of from 20 to 200, preferably from 50 to 150, and especially from 80° to 120° C. In order to obtain a quantitative conversion, it is generally advantageous to use an excess of mercaptocarboxylic acid; however, an epoxide excess may also be employed.

The reaction may be carried out in the presence or absence of a solvent; suitable solvents are liquid, chlorine containing hydrocarbons such as chloroform, carbon tetrachloride or chlorobenzene, aromatic hydrocarbons such as toluene or xylene, or aliphatic hydrocarbons such as hexane, heptane or gasoline fractions.

The reaction may also be carried out in the presence of catalysts; suitable catalysts are iron-III chloride, alkali metal salts of carboxylic acids such as sodium acetate, potassium benzoate or potassium stearate, or ammonium salts of carboxylic acids such as ammonium laurate, triethylammonium octoate or tetraethylammonium stearate. Of course, also the corresponding salts of the mercaptocarboxylic acids used may be employed. The amounts of catalysts are from 0.1 to 5, preferably from 0.5 to 2, parts by weight per 100 parts by weight of mercaptocarboxylic acid ester. The use of catalysts is recommended in the case of epoxides having a poor reactivity; in general, however, the reaction may be carried out without a catalyst. The reaction time is normally from 1 to 10 hours, and the proceeding reaction is controlled by determining the epoxide number.

Some particularly typical representatives of the novel organo-tin compounds are cited below; the invention, however, is not limited to these substances:

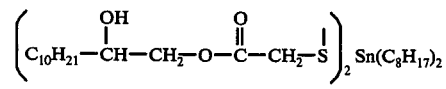
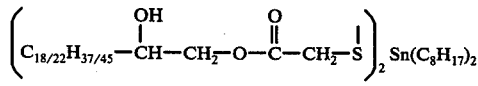
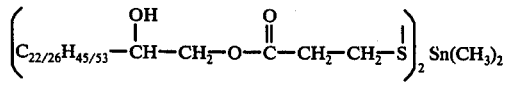

-continued

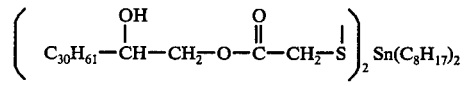
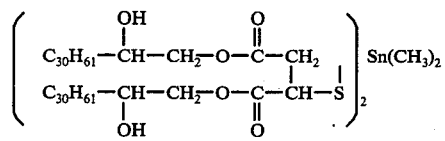
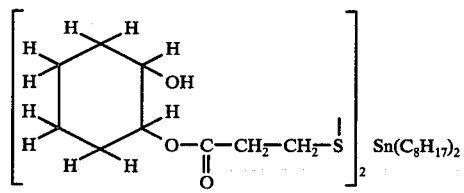
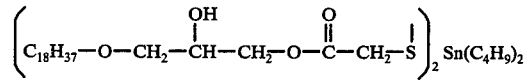

The novel organo-tin compounds may be employed together with other known stabilizers on the basis of metals, stabilizing auxiliaries, antioxidants and UV stabilizers. By metal compounds known as stabilizers (primary stabilizers), there are to be understood organo-tin compounds such as dioctyl-tin-thioglycolates or -carboxylates, furthermore Ba, Sr, Zn, Cd, Mg, Al and Pb soaps of aliphatic carboxylic acids or oxycarboxylic acids having about 8 to 32, preferably 8 to 20, carbon atoms, salts of these metals with aromatic carboxylic acids having preferably from 7 to 12 carbon atoms such as benzoates, phthalates or salicylates or (alkyl) phenolates of these metals and optionally also neutral or basic lead salts of inorganic acids such as sulfuric or phosphorous acid.

Known auxiliary stabilizers (costabilizers) are for example epoxides such as higher epoxidized fatty acids and the esters thereof (for example epoxidized soybean oil, tall oil or castor oil), epoxidized butyl oleate, higher epoxyalkanes or glycidyl ethers, polyols such as pentaerythritol, trimethylolpropane or sorbitol, organic phosphites such as triphenylphosphite, trisnonylphenylphosphite or diphenyl-iso-octylphosphite, or nitrogen containing compounds such as 2-phenylindol. Known antioxidants are for example phenolic compounds such as 2,6-di-tert.-butyl-4-methylphenol or 2,2-(4,4' dihydroxydiphenyl)-dimethylmethane.

The organo-tin compounds of the invention are used in amounts of from 0.05 to 5, preferably 0.1 to 3.0, parts by weight per 100 parts by weight of polymer to be stabilized. The amount of the known primary and costabilizers optionally also present may widely vary. Suitably, the ratio of organo-tin compound of the invention to additional stabilizers in such stabilizer combinations is from 3:1 to 1:10, preferably 2:1 to 1:2.

The organo-tin compounds of the invention are particularly suitable for the stabilization of vinyl halide polymers, that is, organic polymers containing halogen atoms, especially chlorine atoms, linked to the polymer chain. Examples are preferably homopolymers of vinyl chloride and vinylidene chloride, copolymers of vinyl chloride and vinylidene chloride with other ethylenically unsaturated monomers such as vinyl acetate, vinyl propionate, styrene, methylmethacrylate, acrylonitrile, vinyl ether; furthermore unsaturated acids such as maleic, fumaric, acrylic, methacrylic acid and the mono- and diesters thereof with mono- or dialcohols having from 1 to 10 carbon atoms; maleic anhydride; maleimide and the N-substitution products thereof with aromatic, cycloaliphatic or, optionally, branched aliphatic substituents. Also mixtures of halogen containing polymers with other halogen containing or also halogen-free polymers are included as well as mixtures of polyvinyl chloride and ethylene/vinyl acetate copolymers or chlorinated polyethylene.

The polymer may be "hard" or "soft". In the case of "hard" polymers, lubricants, pigments, fillers, impact strength modifying agents etc. may be incorporated besides the above additives. In the case of "soft" polymers, the additives are for example plasticizers such as phthalic, adipic or phosphoric acid esters, polymer plasticizers such as low molecular weight polyesters, chloropolyolefins or also chloroparaffins in some cases. The "soft" polymers of course may contain also the additives cited for "hard" polymers, and furthermore known primary and costabilizers.

The following examples illustrate the invention.

EXAMPLE 1

In a 250 ml glass flask, 36.1 g (0.1 mol) of dioctyl-tin oxide and 100 g (0.2 equivalent) of mercaptoacetic acid ester composed approximately as follows

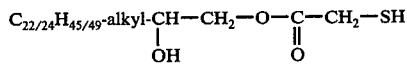

and containing 6.4% of sulfur (obtained from mercaptoacetic acid and epoxide from a α-olefin mixture $C_{24}/C_{26}$) are molten at 75° C. Subsequently, a reduced pressure of 10 mm Hg is established and maintained at 76° – 78° C for 3 hours, and within this period, the reaction water which has formed is taken off via a cooling trap cooled to −80° C.

Yield: 134.0 g (99.6% of the theoretical yield) of a light color, soft, wax-like organo-tin compound having a flow point/drop point of 56°/57° C.

Analysis: 8.7% Sn 4.9% S

EXAMPLE 2

36.1 g (0.1 mol) of dioctyl-tin oxide and 115.0 g (0.1 equivalent) of mercaptoacetic acid ester of approximately the following composition

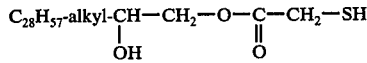

and having a sulfur content of 5.6% are reacted as indicated in Example 1.

Yield: 148.3 g (98.1%) of a light color, wax-like organo-tin compound having a flow/drop point of 74°/75° C.

Analysis: 7.8% Sn 4.3% S

EXAMPLE 3

36.1 g (0.1 mol) of dioctyl-tin oxide and 116.5 g (0.2 equivalent) of 3-mercaptopropionic acid ester having approximately the following composition

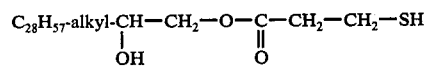

and containing about 5.5% of sulfur are reacted as indicated in Example 1.

Yield: 148.2 g (98.3%) of a light color, wax-like organo-tin compound having a flow/drop point of 78°/79° C.

Analysis: 7.7% Sn 4.2% S

Example 4

36.1 g (0.1 mol) of dioctyl-tin oxide and 154 g (0.2 equivalent) of mercaptoacetic acid ester having approximately the following composition

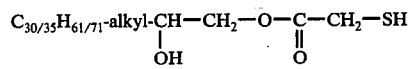

and containing 4.2% of sulfur are reacted as indicated in Example 1.

Yield: 185.5 g (98.5%) of a light color, wax-like, brittle organo-tin compound having a flow/drop point of 86°/86.5° C.

Analysis: 6.3% Sn 3.4% S

EXAMPLE 5 to 14

These examples show the stabilizing effect of the organo-tin compounds of the invention in the processing of polyvinyl chloride. The parts indicated are by weight.

100 parts each of a mass-polymerized polyvinyl chloride having a K value of 67 were homogeneously mixed with 20 parts of dioctyl-phthalate, 0.5 part of a lubricant on the basis of montan wax (montanic acid ester of ethyleneglycol) and the parts of organo-tin compounds as indicated in the following Table 1. For a comparison, the commercial dioctyl-tin-bis-thioglycolic acid isooctyl ester stabilizer was incorporated in Example 14. For determining the dynamic thermostability, the mixtures were applied to a laboratory two-roll mill heated at 175° C, and laminated at 20 rpm to a rough sheet within one minute. In intervals as indicated in the following Table 1, samples were taken from the rough sheets and the color was compared with that of a color scale. The tests were carried out until the rough sheets had become dark brown to black. The numbers of the color scale used represent:

1 = transparent
2 = slightly yellowish
3 = distinct yellow color
4 ° dark yellow to brown
5 ° dark brown to black.

TABLE 1

| Ex. No. | organo-tin-compound according to ex. | parts in the formulation | Dynamic thermostability discoloration of the rough sheet at a laminating time of | | | | | | | | | | | parts of tin in formulation |
|---|---|---|---|---|---|---|---|---|---|---|---|---|---|---|
| | | | 5' | 15' | 30' | 45' | 60' | 80' | 90' | 110' | 120' | 135' | 150' | |
| | | | to color number | | | | | | | | | | | |
| 5 | 1 | 1.0 | 1 | 1 | 1 | 2 | 3 | 4–5 | — | — | — | — | — | 0.087 |
| 6 | 2 | 1.0 | 1 | 1 | 1 | 2 | 3 | 4–5 | — | — | — | — | — | 0.078 |
| 7 | 3 | 1.0 | 1 | 1 | 1 | 2 | 3 | 4–5 | — | — | — | — | — | 0.077 |

TABLE 1-continued

| Ex. No. | organo-tin-compound according to ex. | parts in the formulation | Dynamic thermostability discoloration of the rough sheet at a laminating time of | | | | | | | | | | | parts of tin in formulation |
|---|---|---|---|---|---|---|---|---|---|---|---|---|---|---|
| | | | 5' | 15' | 30' | 45' | 60' | 80' | 90' | 110' | 120' | 135' | 150' | |
| | | | to color number | | | | | | | | | | | |
| 8 | 4 | 1.0 | 1 | 1 | 1 | 2 | 3 | 4–5 | — | — | — | — | — | 0.063 |
| 9 | 1 | 1.8 | 1 | 1 | 1 | 1 | 1–2 | 2 | 3 | 3 | — | 4 | — | 0.158 |
| 10 | 2 | 2.0 | 1 | 1 | 1 | 1 | 2 | 2–3 | 3 | 3 | — | 4 | — | 0.158 |
| 11 | 3 | 2.1 | 1 | 1 | 1 | 1 | 1 | 1 | 1–2 | 1–2 | — | 2 | 3 | 0.158 |
| 12 | 4 | 2.5 | 1 | 1 | 1 | 1 | 2 | 2–3 | 3 | 3 | 3 | 3–4 | — | 0.158 |
| 13 | 1 | 1.3 | 1 | 1 | 1 | 1 | 1–2 | 2 | 3 | 3–4 | 4 | — | — | 0.113 |
| 14 (comp.) | comparative substance*) | 1.0 | 1 | 1 | 2 | 2–3 | 3 | 3–4 | 5 | — | — | — | — | 0.158 |

*)dioctyltin-bis-thioglycolic acid-isooctyl ester

As the Table shows, the organo-tin compounds of the invention, as compared to the known, highly active dioctyl-tin-bis-thioglycolic acid-isooctyl ester, have a similar stabilizing effect at identical amounts in the formulation, but at about half the tin content (Examples 5 to 8, as compared to Example 14). When the amount of organo-tin compound of the invention in the formulation is increased in such a manner that the tin content corresponds to that of the comparative stabilizer used in the test mixture (Examples 9 to 12 as compared to Example 14), the stabilizing effect is improved by about 70%. A considerable improved thermostability is obtained into the plastic composition by means of the compounds of the invention is only ⅔ of that of the Comparative Example (Example 13 as compared to Example 14). Furthermore, the color development of the starting color which is important for the practice is much more favorable in the case of all Examples of the invention, especially Examples 9 to 13, than that of the Comparative Example. Moreover, the molding compositions stabilized by the organo-tin compounds of the invention practically do not stick onto the rolls, while the comparative product displays considerably inferior properties in this respect.

EXAMPLES 15 to 17

These Examples show the stabilizing effect of the organo-tin compounds of the invention with exclusion of the mechanical strain by shearing forces, friction heat and sticking to the surfaces of the rolls (static thermostability in a drying cabinet). In these tests, rough sheets obtained according to the method described for the Examples 5 to 14, but with a laminating time of only 5 minutes, were subjected to a temperature of 175° C in a drying cabinet. The samples were removed at intervals as indicated in Table 2 and evaluated according to their discoloration, as described for the dynamic test. Also in this case, the compounds of the invention proved to be superior to the known stabilizer.

$$\left( R_1 - \underset{\underset{R_2}{|}}{\overset{\overset{OH}{|}}{C}} - \underset{\underset{R_3}{|}}{\overset{\overset{R_4}{|}}{C}} - O - \overset{\overset{O}{\|}}{C} - R_5 - S - \right)_m Sn(R_6)_{4-m}$$

wherein $R_1$ through $R_4$, being identical or different, each represent (a) from 0 to 3 hydrogen atoms,
(b) a phenyl radical or a cycloalkyl or cycloalkylene radical having from 5 to 12 carbon atoms, these radicals optionally being substituted by alkyl group having from 1 to 9 carbon atoms, halogen or -OH,
(c) a linear or branched alkyl radical having from 1 to 100 carbon atoms, optionally substituted by a phenyl, a $C_1$-$C_9$-alkylphenyl, a cycloalkyl or cycloalkylene group having from 5 to 12 carbon atoms;
the radicals cited sub b) and c) optionally containing ether, thioether, carboxylic acid ester or epoxide groups, halogen substituents and C=C bonds in addition, and/or $R_2$ and $R_3$ being common members of a saturated or unsaturated, optionally alkyl- or aryl-substituted alkylene chain having from 3 to 10 carbon atoms; and the sum of all carbon atoms contained in the radicals $R_1$ through $R_4$ being superior to 2 and up to 100;
$R_5$ is an arylene group or a saturated or unsaturated, optionally alkyl- or phenyl-substituted alkylene group having from 1 to 12 carbon atoms in the alkylene chain, the alkyl substituents possibly present in the alkylene chain optionally containing carboxylic acid ester groups,
$R_6$ is a linear or branched alkyl radical having from 1 to 30 carbon atoms, a vinyl, allyl, aralkyl, aryl or cycloalkyl radical having from 5 to 8 carbon atoms, and
m is 1, 2 or 3.

2. Organo-tin compounds as claimed in claim 1, wherein $R_1$ is an alkyl group having from 6 to 58 carbon atoms, $R_2$ and $R_3$ each are hydrogen atoms and $R_4$ a hydrogen atom or a methyl or ethyl group, and the sum

TABLE 2

| Ex. No. | organo-tin compound acc. to Ex. | parts in formulation | Static (= stove) thermostability discoloration of the samples after | | | | | | | | | | | parts tin in formulation |
|---|---|---|---|---|---|---|---|---|---|---|---|---|---|---|
| | | | 5' | 15' | 30' | 45' | 60' | 75' | 90' | 105' | 120' | 135' | 150' | |
| | | | to color number | | | | | | | | | | | |
| 15 | 1 | 1.8 | 1 | 1 | 1 | 1 | 1 | 1 | 1 | 2 | 3 | 4 | 5 | 0.158 |
| 16 | 2 | 2.0 | 1 | 1 | 1 | 1 | 1 | 1–2 | 2 | 3 | 4 | 5 | — | 0.158 |
| 17 | di-octyl-tin bis-thioglycolic acid-isooctyl ester | 1.0 | 1 | 1 | 2 | 3 | 4 | 4 | 4 | 5 | 5 | — | — | 0.158 |

What is claimed is:
1. Organo-tin compounds of the formula of carbon atoms in $R_1$ and $R_4$ is from 6 to 60, $R_5$ is an alkylene chain having 1 or 2 carbon atoms, $R_6$ a methyl, butyl or octyl group and $m$ is an integer of from 1 to 3.

3. Stabilizer for halogen containing polymers consisting of the organo-tin compounds as claimed in claim 1, or containing optionally in addition known primary and/or costabilizers wherein the organo-tin compounds/said known stabilizers ratio range is 3/1 to 1/10.

4. Plastics compositions on the basis of chlorine containing polymers which contain organo-tin compounds as claimed in claim 1 as stabilizers, the amount of said organo-tin compounds being 0.05 to 5 weight parts per 100 weight parts of said polymers.

* * * * *